US011779449B2

(12) United States Patent
Simpson

(10) Patent No.: US 11,779,449 B2
(45) Date of Patent: *Oct. 10, 2023

(54) INFERIOR VENA CAVA FILTER WITH STABILITY FEATURES

(71) Applicant: C.R. BARD, INC., Murray Hill, NJ (US)

(72) Inventor: Charles L. Simpson, West Lake Village, CA (US)

(73) Assignee: C.R. BARD, INC., Murray Hill, NJ (US)

(*) Notice: Subject to any disclaimer, the term of this patent is extended or adjusted under 35 U.S.C. 154(b) by 321 days.

This patent is subject to a terminal disclaimer.

(21) Appl. No.: 16/165,493

(22) Filed: Oct. 19, 2018

(65) Prior Publication Data

US 2019/0117367 A1 Apr. 25, 2019

Related U.S. Application Data

(63) Continuation of application No. 12/519,717, filed as application No. PCT/US2007/087987 on Dec. 18, 2007, now Pat. No. 10,105,206.

(60) Provisional application No. 60/870,722, filed on Dec. 19, 2006.

(51) Int. Cl.
*A61F 2/01* (2006.01)

(52) U.S. Cl.
CPC ...... *A61F 2/0105* (2020.05); *A61F 2002/016* (2013.01); *A61F 2230/005* (2013.01); *A61F 2230/008* (2013.01); *A61F 2230/0078* (2013.01)

(58) Field of Classification Search
CPC ........ A61F 2/01; A61F 2/0103; A61F 2/0105; A61F 2/012; A61F 2002/015; A61F 2002/016

See application file for complete search history.

(56) References Cited

U.S. PATENT DOCUMENTS

| | | |
|---|---|---|
| 4,272,823 A | 6/1981 | Pool |
| 4,494,531 A | 1/1985 | Gianturco |
| 4,643,184 A | 2/1987 | Mobin-Uddin |
| 4,817,600 A | 4/1989 | Herms et al. |
| 4,990,156 A | 2/1991 | Lefebvre |
| 5,059,205 A | 10/1991 | El-Nounou et al. |
| 5,669,933 A | 9/1997 | Chevillon et al. |
| 5,755,790 A | 5/1998 | Simon et al. |
| 5,836,968 A | 11/1998 | Simon et al. |
| 6,007,558 A * | 12/1999 | Ravenscroft ............ A61F 2/01 606/194 |
| 6,217,600 B1 | 4/2001 | DiMatteo |

(Continued)

*Primary Examiner* — Sarah A Long
*Assistant Examiner* — Lindsey Bachman
(74) *Attorney, Agent, or Firm* — Garvey, Smith & Nehrbass, Patent Attorneys, L.L.C.; Charles C. Garvey, Jr.; Fabian M. Nehrbass

(57) ABSTRACT

A filter having a first set of members and a second set of members defining a trap sized to fit into a blood vessel. Each of the first and second members are configured to resiliently extend from the trap. At least one of the first set of members includes a first surface for engaging the vessel wall such that the at least one of the first set of members resists downstream movement within the vessel. At least one of the second set of members includes a second surface for engaging the vessel wall such that the at least one second member resists upstream movement within the vessel.

20 Claims, 6 Drawing Sheets

(56) References Cited

U.S. PATENT DOCUMENTS

| | | |
|---|---|---|
| 6,231,589 B1 | 5/2001 | Wessman et al. |
| 6,258,026 B1 | 7/2001 | Ravenscroft et al. |
| 6,391,045 B1 | 5/2002 | Kim et al. |
| 6,447,530 B1 * | 9/2002 | Ostrovsky ............. A61F 2/0103 606/200 |
| 6,468,290 B1 | 10/2002 | Weldon et al. |
| 6,706,054 B2 | 3/2004 | Wessman et al. |
| 6,972,025 B2 | 12/2005 | WasDyke |
| 7,037,320 B2 | 5/2006 | Brady et al. |
| 8,246,648 B2 * | 8/2012 | Tekulve ................ A61F 2/0105 606/200 |
| 2004/0059373 A1 * | 3/2004 | Shapiro .................... A61F 2/01 606/200 |
| 2004/0158274 A1 * | 8/2004 | WasDyke .............. A61F 2/0105 606/200 |
| 2004/0186510 A1 * | 9/2004 | Weaver ................ A61F 2/0105 606/200 |
| 2005/0045183 A1 | 3/2005 | Callister et al. |
| 2005/0055045 A1 | 3/2005 | DeVries et al. |
| 2005/0131452 A1 | 6/2005 | Walak et al. |
| 2005/0234503 A1 | 10/2005 | Ravenscroft et al. |
| 2005/0234504 A1 | 10/2005 | WasDyke |
| 2005/0267512 A1 | 12/2005 | Osborne et al. |
| 2006/0030875 A1 | 2/2006 | Tessmer |
| 2006/0095068 A1 | 5/2006 | WasDyke et al. |
| 2006/0106417 A1 | 5/2006 | Tessmer |
| 2006/0178695 A1 | 8/2006 | Decant et al. |

* cited by examiner

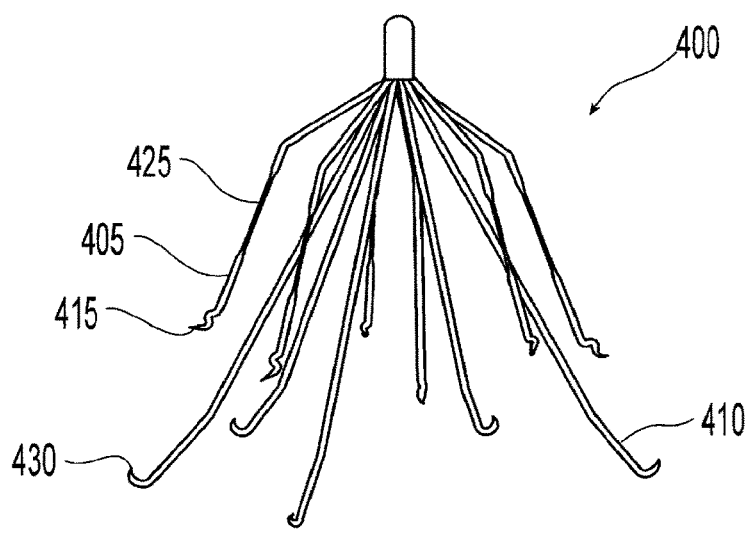
Fig. 6
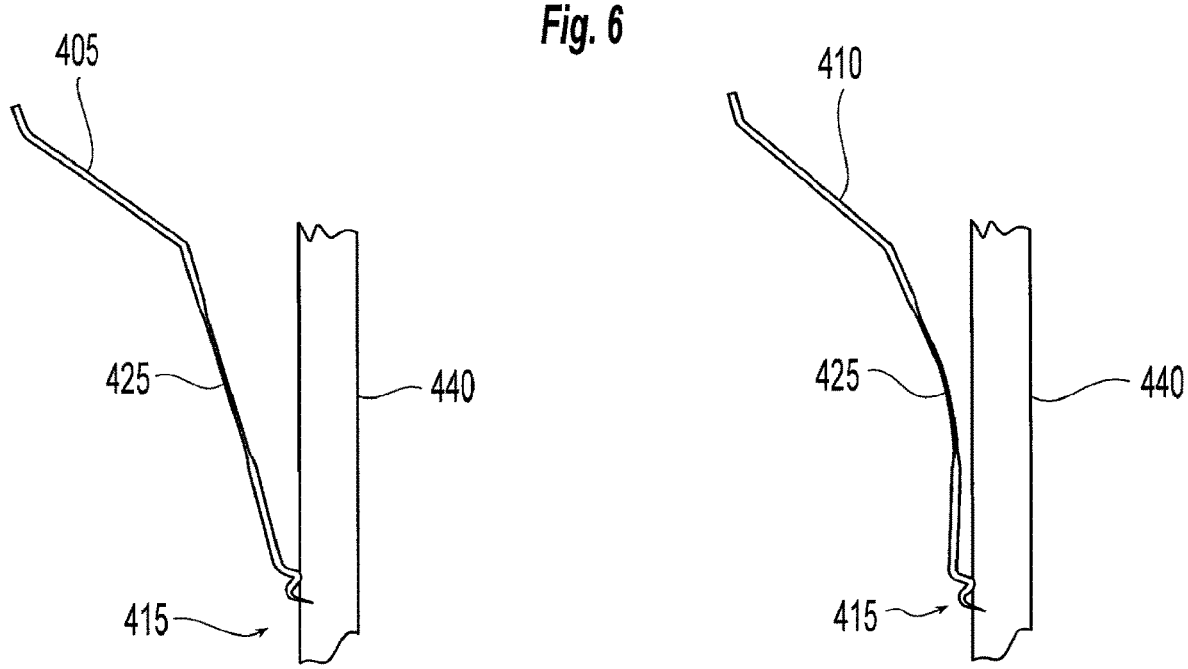
Fig. 7A  Fig. 7B
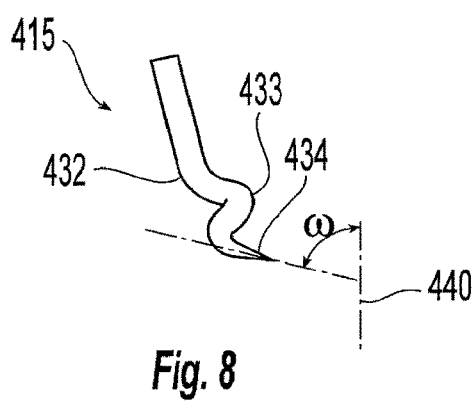
Fig. 8

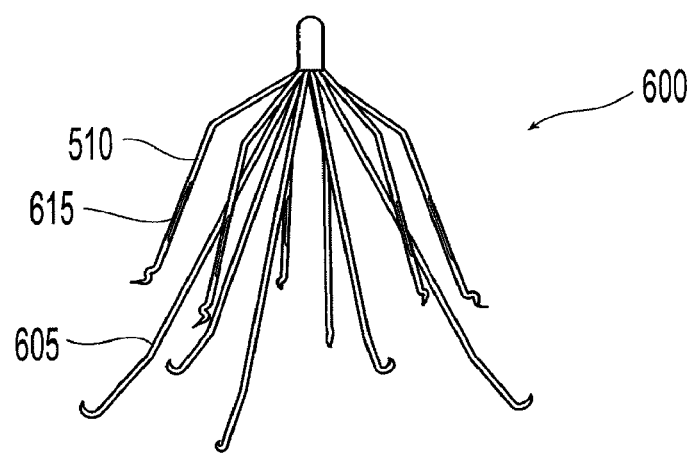
Fig. 11
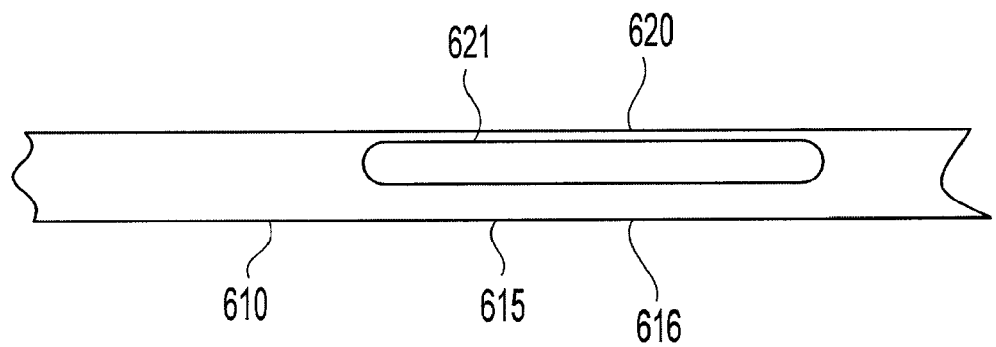
Fig. 12
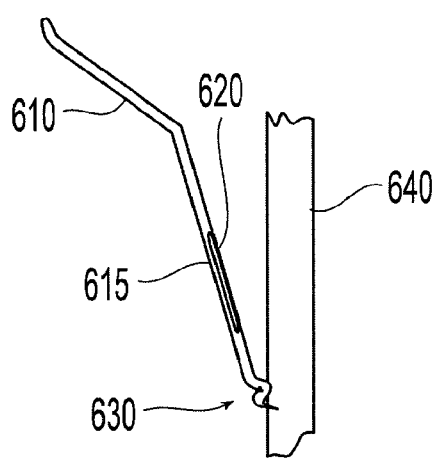 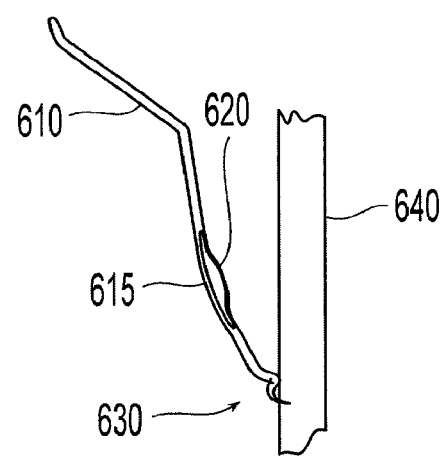
Fig. 13     Fig. 14

INFERIOR VENA CAVA FILTER WITH STABILITY FEATURES

PRIORITY DATA AND INCORPORATION BY REFERENCE

This application is a continuation of U.S. patent application Ser. No. 12/519,717, filed on Jun. 17, 2009 (issued as U.S. Pat. No. 10,105,206 on Oct. 23, 2018), which is a U.S. National Stage Entry of International Application Serial No. PCT/US2007/087987, filed on Dec. 18, 2007, which claims the benefit of priority to U.S. Provisional Patent Application No. 60/870,722 filed Dec. 19, 2006, which is incorporated by reference in its entirety.

TECHNICAL FIELD

The invention relates to a filter device that can be placed via a catheter delivery system in a vessel of a mammalian body to reduce the risk of embolisms. If needed, such filter can be removed from the vessel of a mammalian body without causing traumatic damage to the vessel of a mammalian body. The invention further relates to features that facilitate retrieval and prevent migration of the filter.

BACKGROUND ART

Inferior vena cava filters, also called IVC filters or Greenfield filters, are medical devices that are implanted into the inferior vena cava to prevent pulmonary emboli. They work by trapping emboli while still permitting the flow of blood, thereby preventing an embolus from sealing off a vessel. IVC filters are used if anticoagulation is ineffective or contraindicated.

IVC filters are inserted via the blood vessels (i.e., placed endovascularly). Known filters can be compressed into thin catheters permitting access to the venous system via the femoral vein or the internal jugular vein. A catheter is guided into the IVC using fluoroscopic guidance. The filter is pushed through the catheter and deployed into the desired location. IVC filters are usually positioned just below the junction of the IVC and the lowest renal vein.

IVC filters may be permanent or retrievable. Retrievable filters have a configuration that allows them to be pulled back into a catheter or sheath to be removed. In either case, these filters also include structure to anchor the filter in place within the vena cava. Typical features include elongate diverging anchor elements called second extension elements. These frequently have hooked ends that penetrate the vessel wall to prevent migration within and along the vessel. Some types of filters also have first extension elements which contact the wall of the vessel at a point that is axially displaced from the point of contact by the second extension elements. This apposition helps to keep the filter axially oriented (i.e., prevents tipping) and centered.

U.S. Pat. No. 4,494,531 to Gianturco describes a filter with multiple strands of shape memory wire which are interconnected and wadded together to form a mesh. The filter has projections at either end of the mesh that anchor it within the inferior vena cava. Each anchor has a wire loop act as a stop to prevent the anchors from penetrating too deeply.

U.S. Pat. Nos. 4,643,184 and 4,272,823 to Mobin-Uddin describe a filter with a central cylindrical column which interconnects a pair of corollas of elongate hoops forming two tiers of metal wire. The hoops are each inclined outwardly from the column. Each of loops is formed of two wires with the outer ends of the wires being bent toward each other to form short circumferentially extending portions and then 180° in the same plane to form oppositely extending circumferential portions. The extreme ends of the wires are bent radially outwardly into hooks. The wires of each loop may be joined at the crowns of the open loops to cause them to hook together. The circumferentially bent portions at the ends of the hoops form stops or barriers which prevents the hooks at the ends from penetrating the wall of the passageway (artery) sufficient to prevent a puncture.

U.S. Pat. No. 5,755,790 to Chevillon, et al. describes a filter with a central portion and two corollas connected by the central portion. The upstream corolla has spines with flat shoes at their ends that contact the arterial wall. The support corolla has folded elongate hoops that terminate in v-shaped portion that also contacts the arterial wall downstream of the upstream shoes. The device is removable and does not penetrate the arterial wall.

U.S. Pat. Nos. 6,007,558, 6,258,026, and Publication No. 2005/0234503 to Ravenscroft, et al. describe a filter with first and second corollas joined at the downstream end like the ribs of an umbrella but with one set of ribs forming the downstream corolla and one set forming the upstream corolla. The upstream corolla ribs have hooks at their ends. The downstream corolla rib ends are turned toward the axial center of filter, thereby preventing the ends from projecting into the arterial walls.

U.S. Pat. Nos. 6,231,589 and 6,706,054 to Wessman, et al. describe a filter with first and second corollas connected by a central cylindrical member forming two corollas each with ribs extending radially and upstream. The upstream corolla ribs and downstream ribs have similar structures which bifurcate toward their ends. Barbs are located at the points where the upstream ribs bifurcate to anchor the filter in the artery.

U.S. Pat. No. 6,972,025 to WasDyke describes a filter with first and second corollas joined at the downstream end like the ribs of an umbrella but with one set of ribs forming the downstream corolla and one set forming the upstream corolla. The upstream corolla ribs have hooks at their ends. The downstream corolla rib ends are rounded and made of bioabsorbable material.

U.S. Pat. No. 7,037,320 to Brady, et al. describes a filter with a support which has round wires the form hoops. The hoop formed by the wires ensures that in the expanded position, a filter body will be supported by the support frame in apposition with the interior wall of the blood vessel. The wires have a strain distributing loop that allows the diameter of the hoop to self-adjust to the blood vessel size. The strain relieving loop enhances the compliance of bend points in the circumferential seal of the hoop against the vessel wall.

US Patent Publication No. 2005/0045183 describes a filter with a corolla with extensions having wall-penetrating hook or barb. The extensions form a single array at a single longitudinal location, like the spokes of an umbrella or the legs of a spider.

US Patent Publication Nos. 2006/0030875 and 2006/0106417 to Tessmer describe a filter with first and second corollas joined at the downstream end like the ribs of an umbrella but with one set of ribs forming the downstream corolla and one set forming the upstream corolla. The upstream corolla ribs have hooks at their ends. The downstream corolla rib ends are turned toward the axial center of filter, thereby preventing the ends from projecting into the arterial walls.

US Patent Publication No. 2006/0178695 to Decant, et al, shows a filter with a corolla with extensions having wall-penetrating hook or barb. The extensions form a single array at a single longitudinal location.

U.S. Pat. Nos. 5,669,933 and 5,836,968 to Simon show a filter with a basket and extensions that curve toward the downstream end of the channel.

U.S. Pat. No. 6,468,290 to Weldon, et al, shows a filter with an array of extensions that have hooks that curve toward the downstream direction.

There are a number of conflicting issues concerning the design of vena cava filters. Filters that are intended to be removed must hold their position in the vena cava but in a manner that does not cause undue damage to the vena cava wall. Also, the design features that hold the filter in place must also not promote tissue growth that would make it difficult to remove the filter atraumatically. The filter may need to be self-orienting to some extent as well so there may need to be a bias against the walls of the vena cava to provide this quality.

DISCLOSURE OF INVENTION

According to the exemplary embodiments, there is provided, a vessel-implantable filter of shape memory material with temperature induced austenitic and martensite states which may be easily removed by a single removal device after an extended period of time without significantly injuring the vessel wall. In the exemplary embodiments, the filter is of shape memory material which operates in a temperature induced austenitic state to exert a force on the wall of a vessel by means of oppositely disposed second extension elements to maintain the filter in place, but which may easily be removed after the endothelium layer has covered the ends of the filter second extension elements without significant damage to the vessel wall.

Preferably, a group of first extension elements and a group of second extension elements incline from a central axis. Preferably, also, the ends of the first extension elements in the group of first extension elements are oriented to engage a vessel wall to orient and center the filter in the vessel, and the ends of the second extension elements of the group of second extension elements are oriented to engage the vessel wall to prevent longitudinal movement of the filter along the vessel. More preferably, the ends of at least some of the first extension elements are also configured to engage the vessel wall. For example, the ends of at least some of the second extension elements may be provided with hooks configured to be more elastic than the second extension elements to permit the hooks to straighten in response to a withdrawal force to facilitate withdrawal from the endothelium layer without risk of significant injury to the vessel wall. In preferred embodiments, somewhat different engagement elements can be formed on the ends of at least some of the first extension elements as described below.

Preferably, the hooks are elastic and formed on the free end of an appendage to pierce the vessel wall and insure that the filter remains stable even in response to movement, such as respiratory functions or in the event of a massive pulmonary embolism. The hook is formed to have a maximum migration force, and when subjected to forces below the maximum migration force, the hook retains its shape. When subjected to forces above the maximum migration force, the hook straightens and can automatically disengage without significant damage to the vessel wall.

In a further embodiment, there is provided a vessel implantable filter with a plurality of expandable appendages extending radially away from a central axis such as to contact a cylindrical channel in which the filter is inserted, which contact points are displaced both circumferentially around the axis and axially along the axis. Also, the appendages are urged outwardly by some means, such as by a resilience of the material of which they are made combined with the particular configuration. As a result of the axial displacement of some contact points relative to other contact points, the filter axis aligns with the channel axis. As a result of the radial displacement of the contact points, the filter axis is centered.

In the foregoing embodiment, at least two of the appendages, whose respective contact points are displaced axially relative to one another, have tips that are designed to engage the wall of a vena cava due to the urging thereof. Preferably, this engagement is by way of a sharp tip that penetrates the vena cava wall. Preferably the tip is provided with a stop to prevent more than a predetermined amount of penetration. In this case, preferably, the sharp tips are designed to be capable of only limited penetration force owing to a flexibility of the appendages which causes the appendages to yield, mechanically, when more than the predetermined penetration force is applied. Alternatively, and/or in addition, the tips or the appendages are formed such that when a force is applied in the axial direction, the engaging tips (e.g., the sharp tips) of the appendages flex when more than a predetermined amount of force is applied. In the latter case, this is such as to permit the filter to be withdrawn by applying more than the predetermined amount of force.

In a preferred variation of the foregoing embodiment, the appendages are arrayed in two circular arrays which are offset or spaced along the axial direction. In this case, the appendages at one end may be referred to as second extension elements and the appendages at the other end may be referred to as first extension elements. More preferably, both the first extension elements and the second extension elements have features at their extreme ends which are designed to engage the wall of a vena cava in such a way as to resist axial force. Preferably, the total force the appendages/tips can resist is no more than that required to resist blood flow pressure of 50 mm Hg over the cross-sectional area of the vessel. By providing some support from the first extension elements as well as the second extension elements, the total force per axial-load-resisting contact point is reduced. For example, if the tips are sharp and penetrate the vessel wall, the load per vessel-wall penetration is thereby reduced, causing reduced risk of trauma, particularly upon withdrawal of the filter.

According to another embodiment, a blood clot filter has a trap sized to fit into a blood vessel and configured to hold an embolus. The filter includes wall-contacting members that define and resiliently extend from the trap. A first portion of the wall-contacting members have first surfaces that engage the vessel wall. A second portion of the wall-contacting members have second surfaces that engage the vessel wall. The first surfaces are constructed to engaging the wall in such a manner that the first portion of the wall-contacting elements resist downstream movement due to blood flow even when an embolus is held in the trap; the second surfaces engaging the wall in such a manner that the second portion of wall-contacting elements resist upstream movement.

Preferably, the second surfaces are more effective to prevent upstream movement than to prevent downstream movement. Preferably, each of the second surfaces defines a sharp tip that is angled such that the tip tends to withdraw from the vessel wall if the second portion of the wall-contacting elements is moved in the downstream direction. Preferably, the second portion of the wall-contacting elements are configured to buckle, thereby changing the angles of the sharp tips such that the sharp tips tend to withdraw from the vessel wall on upstream movement. Also, in a variant embodiment, the second portion of the wall-contacting elements are configured to buckle when the filter moves in an upstream direction. Also, in another variant embodiment, the wall contacting surfaces of the first and second portion of the wall-contacting members are axially displaced relative to each other to serve to orient the filter in the blood vessel. In yet another a variant embodiment, the first portion of the wall-contacting members have respective weakened portions that are shaped to limit the amount of radial force the first surfaces apply to the vessel wall.

In the previous embodiment, each of the second surfaces can define a sharp tip and the second portion of the wall-contacting members can include straight and bent portions or be continuously curved. The outward bends present radially-outward surfaces that contact the vessel wall in such a manner as to limit the penetration depth of the respective sharp tips. Preferably, in the latter variant, the second portion of the wall-contacting members are formed by wire extensions and the bent or curved structures have bends at the ends of the wire extensions. In yet another a variant embodiment, the wall-contacting members are configured to fold into a cylindrical package for insertion into and removal from a blood vessel.

According to an embodiment, a blood clot filter has leading and trailing ends and a longitudinal axis. The trap is collapsible toward the longitudinal axis for insertion into a blood vessel and radially expandable outwardly from the longitudinal axis to an expanded configuration to contact and penetrate an inner wall of the blood vessel to provide a downstream migration resisting force. A plurality of elongate, spaced appendages preferably have ends which are centrally interconnected at the longitudinal axis and further have remote ends extending radially away from the longitudinal axis in the expanded configuration of the trap. A first portion of the elongate spaced appendages have pointed hooks formed at the second ends thereof pointing away from the longitudinal axis to engage and penetrate the vessel inner wall in the expanded configuration. Each hook is formed with a maximum migration force such that a force above the maximum migration force applied to the hook as a result of a withdrawal force in excess of the filter migration resisting force applied to the trailing end of the filter in a direction away from the filter leading end will cause the hook to straighten. A second portion of the elongate spaced appendages have multiple protruding portions that indent and protract the vessel inner wall when urged into contact therewith.

In a variant of the above embodiment, the second portion of appendages are repeatedly bent in the radial direction to form undulations that define the multiple protruding portions. In another variant of the above embodiment, the second portion are repeatedly bent in the circumferential direction to form undulations that define the multiple protruding portions. In another variant, the ends of the second portion of appendages are downstream of the ends of the first portion of appendages. In another variant, the first and second portions of the elongate spaced appendages define respective upstream and downstream corollas. In yet another variant of the previous embodiments, the second portions are repeatedly bent in the radial direction to form undulations that define the multiple protruding portions. In yet another variant, the second portion is repeatedly bent in the circumferential direction to form undulations that define the multiple protruding portions. The ends of the second portion of appendages are preferably downstream of the ends of the first portion of appendages.

According to an embodiment, a blood clot filter has a trap having leading and trailing ends and a longitudinal axis, the trap being collapsible toward the longitudinal axis for insertion into a blood vessel and radially expandable outwardly from the longitudinal axis to an expanded configuration to contact and penetrate an inner wall of the blood vessel to provide a downstream migration resisting force. A plurality of elongate, spaced appendages having ends preferably centrally interconnected at the longitudinal axis and further including remote ends extending radially away from the longitudinal axis in the expanded configuration of the trap. A first portion of the elongate spaced appendages have pointed hooks formed at the second ends thereof pointing away from the longitudinal axis to engage and penetrate the vessel inner wall in the expanded configuration. Each hook is formed with a maximum migration force such that a force above the maximum migration force applied to the hook as a result of a withdrawal force in excess of the filter migration resisting force applied to the trailing end of the filter in a direction away from the filter leading end will cause the hook to straighten. A second portion of the elongate spaced appendages have sharp tips with stops that limit the depth to which the sharp tips can penetrate the vessel inner wall.

In a variant of the foregoing embodiment, the second portion of appendages are bent to define the stops. Moreover, the sharp tips of the second portion are preferably aimed in an upstream direction when the filter is expanded and emplaced in the vessel. The sharp tips may be configured such that a downstream movement of the filter causes the sharp tips to withdraw from the vessel inner wall. The ends of the second portion of appendages are preferably downstream of the ends of the first portion. The first and second portions of the elongate spaced appendages preferably define respective upstream and downstream corollas. In an embodiment, the ends of the second portion of appendages are downstream of the ends of the first portion. The first and second portions of the elongate spaced appendages may define respective upstream and downstream corollas.

According to an embodiment, a blood clot filter has a hub extending in a hub direction from a first hub end to a second hub end along a longitudinal axis. A plurality of second extension elements extend away from the second hub end along the longitudinal axis, each of the second extension elements having a second extension element end proximate the hub and a hook at or near a distal end of the second extension element to retain the second extension element to a blood vessel wall. A plurality of first extension elements extend away from the second hub end along the longitudinal axis. Each of the first extension elements has a first end and free end, the first end of each first extension element preferably being contiguous with a portion of the second extension element. In addition, the free end of each first extension element is preferably closer to the axis of the filter than the hook of each second extension element. Moreover, the free ends of each of the first extension elements are preferably spaced equiradially from the longitudinal axis. At least some of the first extension element free ends have features to engage the vessel inner wall to promote stability of the filter.

In a variant embodiment, at least some of the first extension element free ends have features more effective to prevent upstream movement than to prevent downstream movement. In a further variant, each of the at least some of the first extension element free ends having features defines a sharp tip that is angled such that the tip tends to withdraw from the vessel wall if the second portion of the wall-contacting elements is moved in the downstream direction. In yet another variant embodiment, the first extension elements are configured to buckle, thereby changing the angles of the sharp tips such that the sharp tips tend to withdraw from the vessel wall on upstream movement. In the previous embodiment, the first extension elements can be configured to buckle when the filter moves in an upstream direction. The first extension elements may be axially displaced relative to the second extension elements to serve to orient the filter in the blood vessel. In this case, preferably, the first extension elements have respective weakened portions that are shaped to limit the amount of radial force the first surfaces apply to the vessel wall.

According to an embodiment, a blood clot filter has a hub extending in an axial direction with radially extending elements having vessel wall-engaging ends. First radially extending elements have first wall-engaging ends configured to engage a vessel interior wall and thereby prevent downstream movement of the filter. Second radially extending elements having second wall-engaging ends configured to engage a vessel interior wall and thereby prevent upstream movement of the filter. The second radially extending elements are preferably configured to bend more easily in a first direction than a second.

In a variant of the foregoing embodiment, the second radially extending elements preferably have a U-shaped or channeled cross-section, with the interior of the U-shape facing away from the axis of the filter. In another variant, the second radially extending elements are repeatedly bent in the radial direction to form undulations that define multiple protruding portions. Alternatively, the second radially extending elements may be repeatedly bent in the circumferential direction to form undulations that define multiple protruding portions. In a particular embodiment, the ends of the second radially extending elements are downstream of the ends of the first. In the foregoing embodiment, the first and second radially extending elements define respective upstream and downstream corollas.

BRIEF DESCRIPTION OF THE DRAWINGS

The accompanying drawings, which are incorporated herein and constitute part of this specification, illustrate exemplary embodiments of the invention, and, together with the general description given above and the detailed description given below, serve to explain the features of the invention.

FIG. 6 is an isometric view of a filter according to another embodiment of the invention.

FIGS. 7A and 7B illustrate a detail of an first extension element of the filter of FIG. 6 in a narrow and wide channel, respectively.

FIG. 8 is a detailed end view that can be incorporated in any of the extension elements of FIGS. 3A-6.

FIGS. 11-14 show a filter design whose first extension elements buckle when a force is applied in a caudal direction but which are capable of supporting a radial force.

MODE(S) OF CARRYING OUT THE INVENTION

Figure 1:
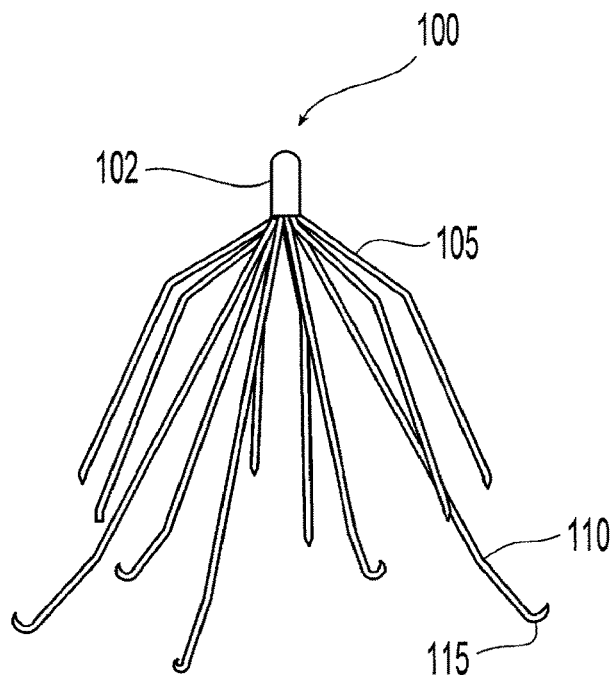
FIG. 1 is an isometric view of a vena cava filter of the prior art.
Figure 2:
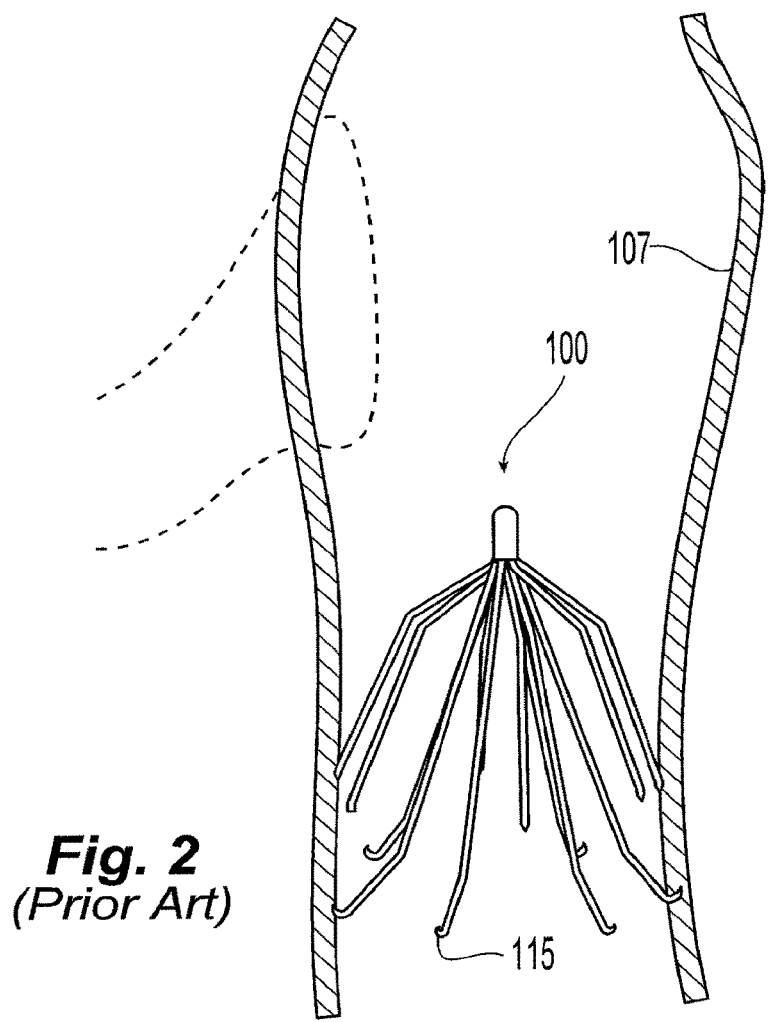
FIG. 2 is an isometric view of the filter of FIG. 1 positioned in a vena cava.

Referring to FIGS. 1 and 2, the filter 100 is shown in an expanded state. Preferably, the filter is made of metal wires held together by a hub where they are joined, for example, by plasma welding. The wires are preferably made of shape memory alloy with a martensite phase that allows the wires to be straightened so as to enable insertion in a catheter and deployment therefrom. In the austenitic phase, the filter recovers to its expanded state, which is illustrated.

The filter 100 has a double basket or trap design with first extension elements 105 forming one basket or trap and second extension elements 110 forming a second basket or trap. Each of the extension elements 105, 110 have one end substantially centrally interconnected at the longitudinal axis of the filter 100 and a remote or distal end that extends radially away from the longitudinal axis. Alternatively or in addition to, where the centrally interconnected ends of the extensions elements 105, 110 are axially spaced along the filter axis (not shown) the filter can present axially spaced corollas, one upstream and one downstream. Both the first extension elements 105 and second extension elements 110 engage the walls of the vena cava 107 after deployment. The second extension elements contain hooked ends 115 that penetrate the vena cave 107 wall and prevent the filter 100 from moving downstream due to the frictional force of blood moving past it. Preferably, the hooked ends 115 are configured to yield upon the application of a specified amount of force to ameliorate retrieval.

Figures 3A, 3B:
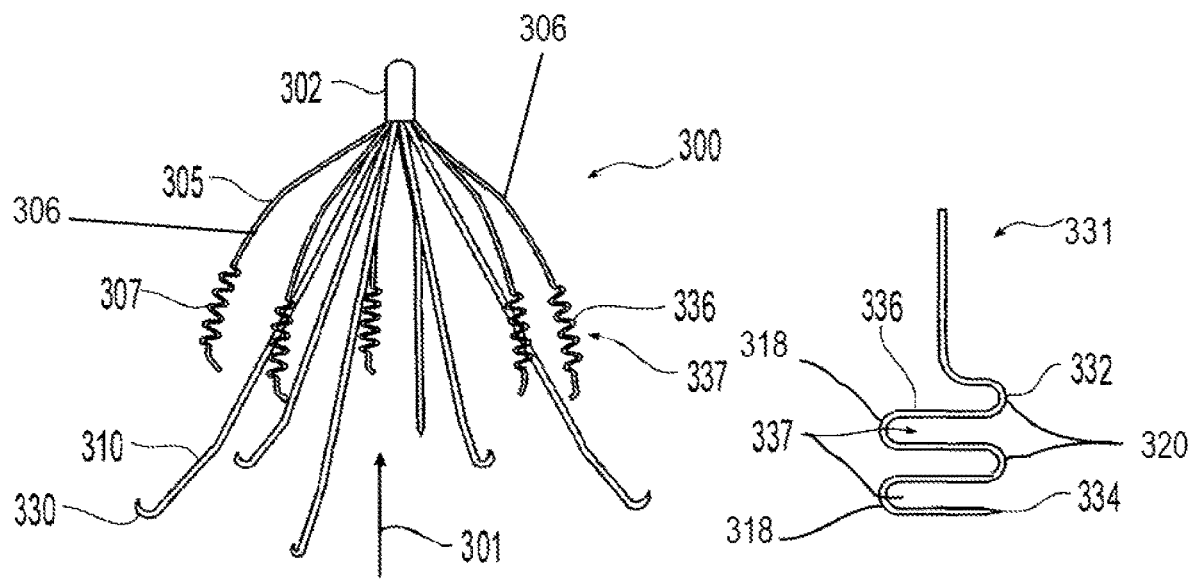
FIG. 3A is an isometric view of a filter according to an embodiment of the invention.
FIG. 3B illustrates an alternative extension element that has a surface with protrusions and recesses.

Referring to FIG. 3A, a vena cava filter has first extensions 305 that have spacing portion 306 and multi-protrusion surface part 307 and second extensions 310 with engagement elements 330. As shown in FIG. 3A, each protrusion is closer to the distal end of the extension than to the proximal end of the extension. In the example shown, the multi-protrusion surface part 307 is a wire that undulates in a radial direction toward and away from a radial center aligned with the filter axis, which may further define the axis of blood flow as indicated by the arrow 301. The multi-protrusion surface part 307 may take other forms. For example the multi-protrusion surface part 307 could also include an engagement element 331, as shown for example in FIG. 3B, with a portion 332 near the end 334 that undulates preferably in the circumferential direction about the filter axis. The particular shape of the undulations depicted in the embodiment of FIG. 3B may vary. For example, they may not be 90° and 180° bends but could be greater than or less than these such as to define diagonal traverses in the circumferential direction. FIG. 3B also shows convexly curved portion 320, protrusions 332, recesses 337, and connecting portions 318. In addition, in any of the embodiments described thus far, the wires need not have circular cross-sections, but could have ellipsoidal, oval, rectangular, or other cross-sectional shapes and could also be hollow or intermittently hollow. In addition, the wires could be composite structures with a skin of one material and a core, which could also be hollow, of another material. By "composite" the inventor does not intend to limit the embodiments to structures with fixed elements, such as fibers in a polymer matrix. Rather composite structures could have multiple movable or non-movable elements. Some particular examples of different structures are disclosed below in connection with specific functional enhancements. Both of these configurations 300 and 331 create indenting portions 336 and gaps or recesses between them that cause tissue to protract as discussed with reference to FIGS. 4A and 4B, below.

Figures 4A, 4B:
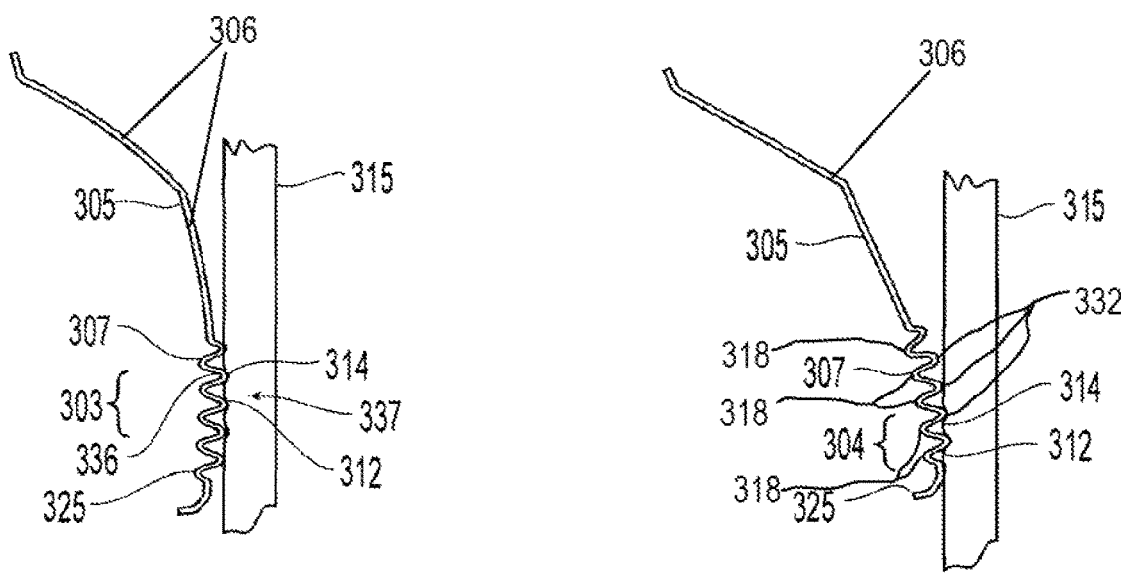
FIGS. 4A and 4B illustrate a detail of an first extension element of the filter of FIG. 3A in a narrow and wide channel, respectively.

Referring to FIG. 4A, the multi-protrusion surface part 307 when pressed against the vena cava wall 315 by the urging force of the attached first extensions 305, protracts the tissue of the wall slightly as indicated at 312. This tissue protraction and indentation resists the tendency of the first extension element to "ski" along the wall thereby resisting any migration. See, for example FIG. 4B, showing protrusions 332 and connecting portions 318. Migration in the cranial direction may be resisted by engagement elements 330 that penetrate, such as for example, hooks 330 that withstand the force of flowing blood. However, it may be desirable to achieve greater stability, without interfering with the function of the filter or health of the patient. The feature 307 in the first extensions 305 resists such movement and also helps to resist movement in the cranial direction by the same mechanism. By assisting in the resistance of movement in the cranial direction, the feature 307 may reduce the load on tissue resulting from the penetration of the hooks 330 on the second extensions 310. As a result, the risk of trauma caused by cranial force on the tissue engaged with the penetrating elements such as hooks 330 may be reduced. To exploit this advantage, the yield threshold of the hooks 330 may be lowered. Note that other penetrating elements may be employed such as disclosed in the prior art, for example, barbs, edged shoes (e.g., as described in U.S. Pat. No. 5,755,790), or roughened surfaces.

Note that not all of the second extensions 310 need have hooks 330 provided on them. For example, barbs or roughened surfaces that permit tissue growth over them could be used. However, it is preferred to use a feature that is immediately effective such as a barb, hook, or shoes with edges, since the device may need to resist the forces of the cranial flow immediately after implantation.

The multi-protrusion surface feature 307 provided on the first extension elements 305, as seen for example in FIG. 3A, can alternatively be implemented on some of the second extension elements 310, or further in the alternative, in a combination of the second extension elements 310 and first extension elements 305. Preferably, first extension elements 310 with the multi-protrusion surface feature 307 would not have hooks. Referring particularly to FIGS. 4A and 4B, the multi-protrusion surface feature 307 of the first extension elements 310 are curved so that when the filter 300 is narrowly confined, a middle or upper portion 303 of the multi-protrusion surface feature 307 presses against the vena cava wall 315 and when the filter 300 is in a wider channel, a region 304 closer to the end 325 presses against the vena cava wall 315. The discussion of this paragraph applies to the engagement element 331 of FIG. 3B as well.

Although six first extension elements 305 and six second extension elements 310 are illustrated, there can be a different number. For example, preferably the number is at least three of each, and more preferably, there may be four to twelve first extension elements 305 and/or four to twelve second extension elements 310. The first extension elements 305 and second extension elements 310 may be symmetrically arrayed about the hub 302 or asymmetrically arrayed thereabout, however this is not essential. Since the materials are very resilient, the overall shape will conform with the anatomy of the patient being treated. Also, varying the lengths of the first 305 and second 310 extension elements may be useful for most particular embodiments if the end features, such as hooks, are prone to interfere with each other when the device is packed in a catheter for delivery. However, the material of which the extension elements are made may be a shape-memory material that allows the hook and undulating parts to assume a straight configuration that ameliorates packaging.

Although hooks 330 are an extension element feature that can prevent downstream movement within a vessel, i.e. in the cranial direction of the filter, other engagement features can be employed. For example, the extension elements may include one or more barbs located at or near their ends in order to engage the vena cava wall. Such an engagement feature need not need not necessarily taper, as is the case with a hook that preferably tapers to a point. Instead, it may be sufficient for a constant diameter portion of the engagement element to have a bend which turns toward the wall of the vena cava. Further in the alternative, tractive resistance may be supplied with no end hooks or barbs if the radial forces in the extension elements are sufficient to provide the needed resistance. Note further that the extension elements need not collectively taper to form the trap as seen, for example, in FIG. 3A. For example, it would be sufficient for the extension elements to serve the function of assisting in orienting the filter if there are contact points that are relatively displaced in the flow direction.

Figure 5A:
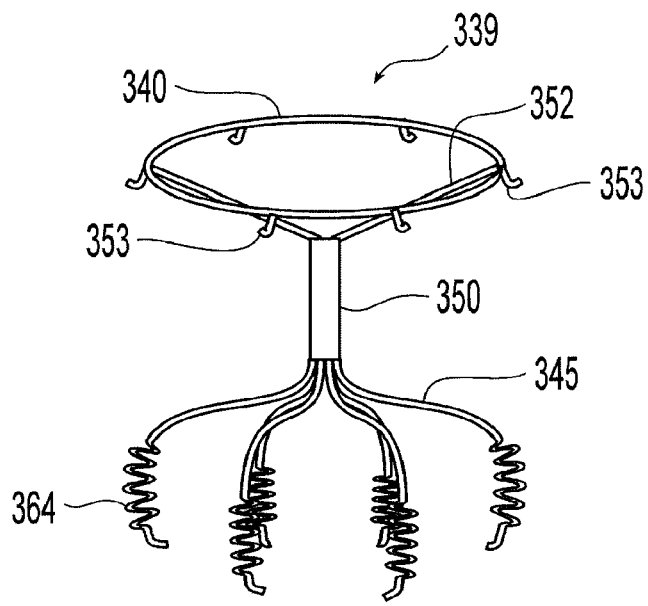
FIGS. 5A-5D illustrate various alternative configurations for providing a feature that protracts and indents the vena cava wall to provide tractive resistance to migration.
Figure 5B:
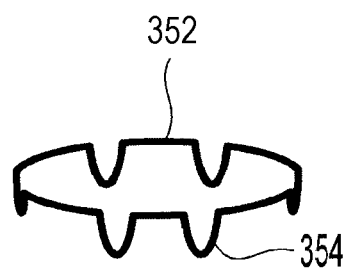

Although in the embodiment of FIG. 3A, the first extension elements 305 are the portions of the filter 300 whose contact portions (e.g., 303, 304 in FIGS. 4A and 4B) are at the cranial-most end of filter 300, the multi-protrusion surface parts 307 can be located such that the multi-protrusion surface parts 307 are at the caudal end of the filter or both the caudal an cranial ends of the filter as well, as seen for example, in FIG. 5A. Also, the supporting features of the filter do not need to be extending first extension elements as in the embodiment 300. They can assume other shapes that provide the functions of the orienting and engaging function of the multi-protrusion surface part 307. Also, a complementary component that engages the vena cava wall need not be provided on extensions that stem from a hub like branches of a tree. The filter 339 of FIG. 5A illustrates such alternatives. In the filter 339, a flexible hoop 340 has hooks 353 attached thereto which engage the vena cava wall. Preferably, the hoop 34 is flexible so as to allow conformance with a range of vena cava sizes. The flexibility may be augmented by providing relief portions 354 of an alternative hoop 352 structure as shown in FIG. 5B. Multi-protrusion surface parts 364 are provided on extensions 345. The hoop 340 is joined to the extensions 345 by a hub 350 located near the axial middle of the filter 339. More specifically, the hub 350 is preferably an elongate tubular member having a first hub end and a second hub end axially spaced from the first hub end along the axis of the filter 339. The first hub end is preferably joined to the hoop 340 and the second hub end is preferably joined to the extensions 345 to couple the extensions 345 to the hoop 340. Due to their relative orientation, the extensions 345 and the hoop 340 can provide upstream and downstream corollas.

Figure 5C:
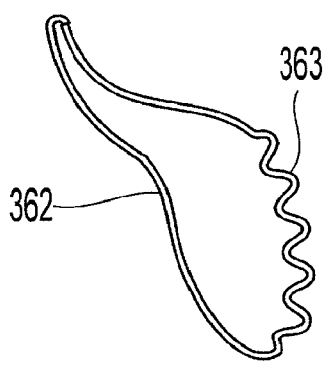
Figure 5D:
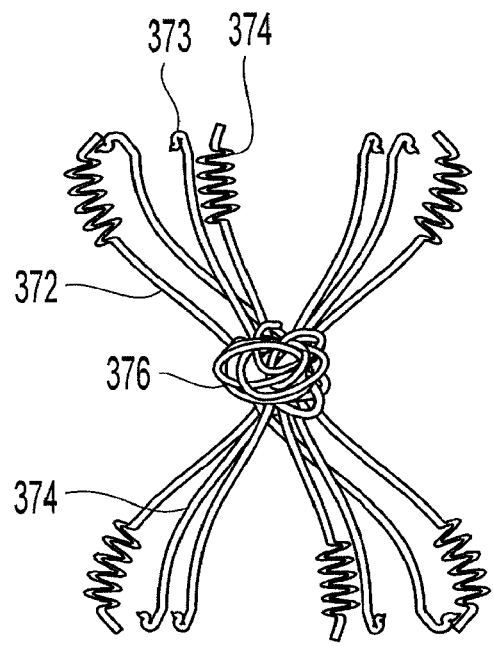

Note that in the filter 339, the movement resisting hooks 353 are positioned to make contact with the vena cava at cranial-most contact points while the multi-protrusion surface parts 364 are located to make the caudal-most contact points of the filter 339. Also, the extensions 345 that define the multi-protrusion surface parts need not be open ended structures, for example, as shown in FIG. 5C, a loop 362 can present the contact feature such as the multi-protrusion surface parts 363 or other contact structure sufficient to provide the desired tractive resistance. Finally, the filter need not be configured such that the types of contact features, whether soft-engaging, i.e., tractive resistant or frictional, such as multi-protrusion surface parts or hard-engaging, i.e. penetrating, such as hooks, are located at opposing ends of the filter. For example, as shown in FIG. 5D, hooks 373 and multi-protrusion surface parts 374 can be co-located at both ends (or alternatively, one end, which is not depicted). Also, there need not be a separate hub or other elements to tie the extensions 372 and 374 together. For example, as shown, a tangle 376 of the extensions 372 and 374 may serve that function.

Referring now to FIG. 6, in another exemplary embodiment of a filter 400, first extension elements 405 and second extension elements 410 preferably carry respective engagement elements 415 and 430 which are preferably configured as hooks as shown. In this case, the shapes of the first extension element hooks 415, which resist any force in the caudal or upstream direction, are shaped to limit the penetration depth as shown in FIGS. 7 and 8. Also, the hooks 415 are shaped to serve the caudal force-resisting function. Accordingly, as shown in FIG. 8, the hooks 415 are shaped such that they project into the vena cava 440 wall and define an angle ω therewith so that upon any cranial movement, they tend not to dig further in or alternatively configured to withdraw. Thus, the extreme tips 434 of the hooks 415 are angled slightly toward the caudal direction such that the angle ω is preferably made acute. To limit the penetration depth of the tips 434, a stop may be provided. The stop is preferably formed by a tight radius bend defining an acute undulation or knee-shaped structure 433 adjacent the hook 415. The surface of the knee shaped structure 433, upon contact with the vena cava wall 456, stops or limits the tip 440 from penetrating deeply into the wall 456. Alternatives such as a bulge or plate at the end of the extension element may also be used as a stop provided it acts to limit the penetration of the tip 440 into the wall 456.

The feature of FIG. 8 may be used in place of the any of the aforementioned multi-protrusion surface features. The radial force applied to the hook 434 feature may be limited by providing a weak buckling portion 425, with a flattened or smaller cross-sectional area than the rest of the extension element. The buckling portion 425 preferably bends radially outward as shown in FIG. 7B when more than a predetermined amount of radial (and axial) force is applied urging the tip 415 into the vena cava wall.

Figure 9A:
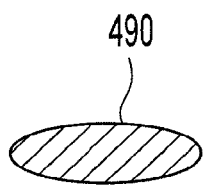
FIGS. 9A and 9B show an first extension element of a further embodiment of the invention, FIG. 9A in cross section and 9B from the side.
Figure 9C:
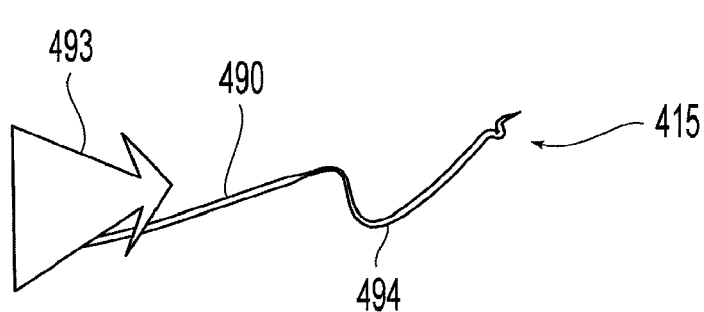
FIG. 9C shows the embodiment of a FIG. 9A in an axial direction as it bends in response to a force aligned in a caudal direction.
Figure 9B:
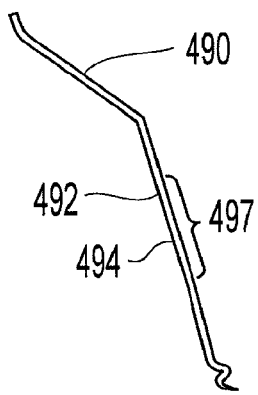

A limit on the amount of force that must be withstood by the vena cava can be imposed by suitably configuring the extension element 405, 410. For example, the extension element 410 can be shaped so as to preferably buckle when a threshold exceeding caudal force (schematically indicated by arrow 493 in FIG. 9C) is applied to it. Accordingly, the extension element would be configured to apply a limited radial force to the vena cava wall, and moreover would be limited in the penetrating force with which the tip can be urged into the vena cava wall 440. On exemplary shape for buckling is shown in FIG. 9A. The cross-sectional shape of an extension element 490 can have a large aspect ratio, such as an elliptical portion 494 extends a substantially linear portion 497 of the extension 490. If the long axis of the ellipse is aligned with the radial direction, the extension 490 can apply a significant radial force. But if a caudal force is applied to the filter a major component of the force will be along the length of the thin extension 490 in the axial direction which is suitable to cause the extension 490 to buckle as shown in FIG. 9B in which the extension 490 is shown looking from the cranial end of the filter in an axial direction toward the caudal direction where the tip 415 terminates the extension 492.

Figure 10A:
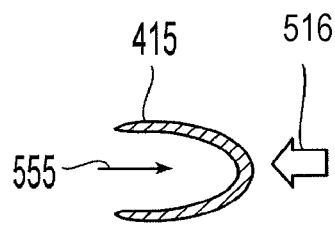
FIGS. 10A through 10C show an extension element that permits force to be applied in a radial direction, but which buckles when too much force is applied in a caudal direction with FIGS. 10A and 10B showing the extension in cross-section and FIG. 10C showing the extension in plan view.
Figure 10B:
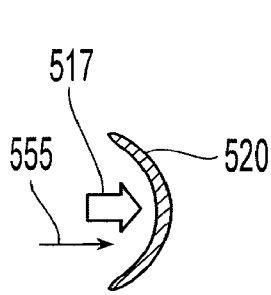
Figure 10C:
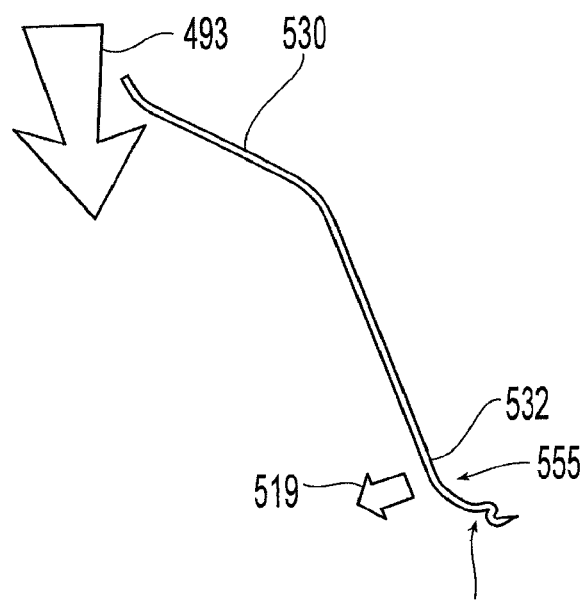

FIGS. 10A to 10C illustrate an alternative mechanism for limiting the caudal force that can be transmitted through a filter extension 530 to the tip 535 of the extension 530. In this embodiment, the cross-section resists bending in one direction as illustrated by arrow 516 but is relatively easy to bend in the other direction as illustrated by arrow 517. In the illustrated embodiment, the extension has a U-shaped cross-section extending along a portion 532 of the extension 530. The recess 555 of the portion faces away from the axis of the filter. If a caudal force is applied, the extension 530 will bend as illustrated in FIG. 10C by the arrow 519. This rotates the tip 535 so that it is not urged further into the vena cava wall. Note that a V-shaped cross-section or any other channeled configuration may be used provided that it is effective to limit the caudal force transmitted through the filter extension 530 to the tip 535. Another alternative is illustrated in FIGS. 11 through 14 in which a portion 615 of the extensions 610 have slots 621 in the extensions 610 that are located to define a thick bridge 616 and a thin bridge 620. As a result of this structure, which may be flat or round in cross-section, if a caudal force is applied through the extension 610, the thin bridge 620 is forced to resist a compressive force along its length, which, because the thin bridge 620 is thin, cannot be withstood beyond a threshold. Thus, the portion 615 bends as shown in FIG. 14. As shown in FIG. 13, when a radially outward (toward the vena cava wall 640) force is applied through the extension 610, the thin bridge 620 acts in tension and can sustain a substantial force allowing the extension 610 to apply the radial force against the vena cava wall 640. The tip 630 may be as in the foregoing embodiments.

As discussed, while it is possible that the filter could be made from ductile metal alloys such as stainless steel, titanium, or elgiloy, it is preferable to make it from Nitinol. Nitinol is a low modulus material which allows the extensions of the device to be designed to have low contact forces and pressures while still achieving sufficient anchoring strength to resist migration of the device. The force required to cause the discussed buckling and yielding behavior can be adjusted to the total force required to resist filter migration in the respective direction. This can be accomplished by changing the cross sectional area or geometry of the extensions, by material selection, or a combination of these.

The force or stress which is required to deform the various deformable portions can be correlated to the force applied to such part under the threshold load conditions. For example, this may correspond to normal human peak blood pressure multiplied by a maximally occluded condition of the filter.

The preferred embodiment corresponds substantially to filter structures in which first extension elements and second extension elements extend from a common hub. In that embodiment, the stabilization features may be provided on the first extension elements. Thus, in the present specification where an embodiment of an extension is discussed without reference to a specific structure and the extension provides a stabilization function, it is preferred that the feature be provided on the first extension elements 105 of a device having a general configuration as that of FIG. 1. In such an embodiment, the first extension elements 105 aid in centering and provide a secondary filtering level. The first extension elements are preferably curved such that the ends of the first extension elements are bent inwardly. The curved parts minimize the possibility of the first extension element engaging the vena cava wall or side branches and the length of the first extension elements reduces the possibility of the first extension element being bent upward. The migration resisting features may be employed on a single first extension element or any or all of the first extension elements, preferably six in number.

Again, regarding the preferred general filter configuration, the multi-protrusion surface feature can be created by locally bending the wire at intervals along the length of the first extension element. By adding the protrusions along the length of the first extension element they will provide resistance in a both small in large vena cavas. In the embodiments with tip hooks that resist caudal forces, the engagement force is controlled by two mechanisms. First, the extension element has a penetration depth stop which limits the penetration into the wall. Second, the extension element is designed to buckle or collapse at a predetermined load in order to limit the amount of penetration force. One or both of these design features can be used to control the engagement with the wall. The first extension element is preferably designed to center the filter by applying a sufficiently high radial force component. The stabilization features may employ one or more first extension elements.

While the present invention has been disclosed with reference to certain embodiments, numerous modifications, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

The invention claimed is:

1. A blood clot filter configured to be implanted within a vessel having a vessel wall surrounding a blood vessel channel filled with blood that flows in a downstream direction, comprising:
 a) a trap having leading and trailing ends and a longitudinal axis, the trap being collapsible toward the longitudinal axis for insertion into a blood vessel and radially expandable outwardly from the longitudinal axis to an expanded configuration to contact and penetrate an inner wall of the blood vessel to provide a downstream direction migration resisting force;
 b) the trap having a plurality of elongate, spaced members having ends centrally interconnected at the longitudinal axis and remote ends extending radially away from the longitudinal axis and toward said trailing ends in the expanded configuration of the trap;
 c) said plurality of members including a first plurality of elongate spaced members having a first anchor that includes a hook pointing away from the longitudinal axis to engage and penetrate the vessel inner wall in the expanded configuration, each hook retarding movement of the filter in a downstream direction, each hook formed with a maximum migration force such that a force above the maximum migration force applied to the hook and in a direction opposing the maximum migration force will cause the hook to straighten;
 d) said plurality of members including a second plurality of members, each said member of said second plurality having a member proximal end and a member distal end, a length and a second anchor that retards movement of the filter in an upstream direction, said second anchor includes multiple protruding portions next to the member distal end that are configured to engage the vessel wall next to said trailing ends in said expanded configuration;
 e) recesses in between said protruding portions, each protruding portion having a convexly curved outer portion that is positioned to engage the vessel wall, each protruding portion connected to another protruding portion with a curved connecting portion, wherein said recesses and connecting portions do not engage the vessel wall;
 f) wherein each said member of said second plurality has a generally linear section that extends proximally of said protruding portions;
 g) the most distal of the protruding portions engaging the vessel wall for vessels having wider channels;
 h) the most proximal of the protruding portions contacting the vessel wall for narrower channels; and
 i) wherein each protruding portion is closer to the member distal end than to the member proximal end.

2. The blood clot filter of claim 1 wherein a majority of the generally linear section is spaced proximally away from said protruding portions.

3. The blood clot filter of claim 1 wherein there is a spacing portion of each member of said second plurality that is not a part of said protruding portions, said spacing portion located proximally of said protruding portions.

4. The blood clot filter of claim 1 wherein each member of the second plurality has an upper section, a bend, and said generally linear section positioned distally of said bend.

5. The blood clot filter of claim 1 wherein the second plurality of members are repeatedly bent in the radial direction to form undulations that define the multiple protruding portions.

6. The blood clot filter of claim 1 wherein each of the members of the first plurality are longer than each of the members of the second plurality.

7. The blood clot filter of claim 1 further comprising a hub and wherein each member of the first plurality is connected to the hub.

8. The blood clot filter of claim 1 further comprising a hub and wherein each member of the second plurality is connected to the hub.

9. The blood clot filter of claim 1 wherein each member of the first plurality has a bend.

10. The blood clot filter of claim 9 wherein the bend is spaced proximally away from the hook.

11. The blood clot filter of claim 9 further comprising a hub, wherein each member of the first plurality is connected to the hub and wherein the bend is spaced in between the hub and the hook.

12. The blood clot filter of claim 9 wherein the bend is spaced closer to the longitudinal axis than the hook.

13. The blood clot filter of claim 1 wherein each member of the second plurality has a bend.

14. The blood clot filter of claim 13 wherein the bend is spaced proximally away from the protruding portions.

15. The blood clot filter of claim 13 further comprising a hub, wherein each member of the second plurality is connected to the hub and wherein the bend is spaced in between the hub and the protruding portions.

16. The blood clot filter of claim 15 wherein the bend is spaced closer to the longitudinal axis than the protruding portions.

17. The blood clot filter of claim 13 wherein the bend is spaced closer to the longitudinal axis than the protruding portions.

18. The blood clot filter of claim 1 wherein the plurality of members define respective upstream and downstream corollas.

19. The blood clot filter of claim 1 wherein multiple of said protruding portions engage the vessel wall for vessels having wider channels.

20. The blood clot filter of claim 1 wherein multiple of said protruding portions engage the vessel wall for vessels having narrower channels.

\* \* \* \* \*